(12) United States Patent
Krawetz et al.

(10) Patent No.: US 6,279,385 B1
(45) Date of Patent: Aug. 28, 2001

(54) DETERMINATION OF ISOTHERMAL SECANT AND TANGENT BULK MODULES

(75) Inventors: Arthur A. Krawetz, Evanston; Phat A. Phan, Skokie; Pricha Klinsuttho, Elmwood Park, all of IL (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/303,742

(22) Filed: May 3, 1999

(51) Int. Cl.[7] .............................. G01N 11/00; G01N 11/08
(52) U.S. Cl. .............................. 73/53.01; 73/54.06
(58) Field of Search .................. 73/53.01, 54.01, 73/54.06, 54.14, 54.41; 356/70, 246; 702/54

(56) References Cited

U.S. PATENT DOCUMENTS

| | | | |
|---|---|---|---|
| 3,836,412 | * 9/1974 | Bousany et al. | 156/62.2 |
| 4,113,384 | * 9/1978 | Lauer et al. | 356/70 |
| 4,193,291 | * 3/1980 | Lynnworth | 73/32 A |
| 4,384,472 | * 5/1983 | Tournier | 73/30.01 |
| 4,559,810 | * 12/1985 | Hinrichs et al. | 73/54.41 |
| 4,862,384 | * 8/1989 | Bujard et al. | 702/54 |
| 5,383,352 | * 1/1995 | Krawetz et al. | 73/54.01 |
| 5,594,546 | * 1/1997 | Westerfield et al. | 356/246 |
| 5,734,093 | * 3/1998 | Miller, Jr. | 73/30.03 |
| 5,775,049 | * 7/1998 | Fricke | 52/720.1 |

* cited by examiner

Primary Examiner—Hezron Williams
Assistant Examiner—Jay L. Politzer
(74) Attorney, Agent, or Firm—William G. Auton

(57) ABSTRACT

A method to measure both the isothermal secant and tangent bulk modules and the density of functional fluids. The instrumentation and methodology described in this invention use much smaller volumes of fluids which permits the measurement of these critical properties on experimental fluids which are available in only limited quantities.

1 Claim, 2 Drawing Sheets

DETERMINATION OF ISOTHERMAL SECANT AND TANGENT BULK MODULES

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to fluids, on more specifically the invention pertains to a system and method to measure both the isothermal secant and tangent bulk modules and the density of functional fluids. The instrumentation and methodology described in this invention use much smaller volumes of fluids which permits the measurement of these critical properties on experimental fluids which are available in only limited quantities.

Bulk modulus is a property which describes the resistance of a liquid to compression. It is a reciprocal of compressibility. It may be determined by either isothermal (static) or adiabatic (dynamic or isentropic) methods. In either case, bulk modulus may be expressed as either secant or tangent functions.

The hydraulic systems required by modern aircraft and missile systems operate at temperatures and pressures which have become increasingly more elevated in response to the demands for increased performance. As a result, the need for the determination of physical properties at high pressures and temperatures has become a requirement of critical proportions. Specific needs include measurement of density, tangent bulk modulus, secant bulk modulus and viscosity.

The best example of prior art systems is in U.S. Pat. No. 5,383,352, dated Jan. 24, 1995, entitled Method for the measurement of bulk modules and pressure viscosity of liquids, Krawetz, Arthur A., the disclosure of which is incorporated herein by reference. This reference describes a method for determining bulk modulus of a liquid based on a pressure-volume-temperature relationship at constant volume corrected for changes in system volume due to elevate pressure and temperature. The apparatus used to determine bulk modulus comprises a pressure vessel in which the liquid to be tested is introduced, and from which all gases are removed. The vessel is placed in a constant temperature oven and the pressure is records.

The above-cited reference is a patent method for the measurement of bulk modulus and pressure viscosity of liquid. The method is based on a pressure-volume-temperature relationship at a constant volume. The apparatus comprises a constant temperature oven, a container vessel within the oven, a plurality of valves, a pump, a regulator and a viscometer. The apparatus is used to obtain a relationship expressing vessel volume at any specified temperature and pressure. This relationship is then used to determine bulk modulus and pressure viscosity.

Other prior art systems include the following U.S. patents, the disclosures of which are incorporated herein by reference:
U.S. Pat. No. 4,113,384 issued to Lauer et al.
U.S. Pat. No. 4,113,384 issued to Lauer et al.
U.S. Pat. No. 4,193,291 issued to Lynnworth
U.S. Pat. No. 4,384,472 issued to Tournier
U.S. Pat. No. 4,559,810 issued to Hinrichs et al.
U.S. Pat. No. 5,383,452 issued to Krawetz.

SUMMARY OF THE INVENTION

The present invention includes a novel method for the direct determination of isothermal secant bulk modulus over the pressure range from ambient to 15,000 psi. Once the relationship between secant bulk modulus and pressure has been determine over a given range of pressure, it is possible to calculate the tangent bulk modulus and sample density within the same region. In this calculation it is assumed only that, at constant temperature, isothermal secant bulk modulus is a linear function of pressure. This assumption has been repeatedly verified by experimental data. No significant expectations have been noted. Isothermal secant bulk modulus data may also be employed to determine density as a function of pressure. Density data determined as a function of pressure may be use to convert dynamic viscosity data to kinematic viscosity. In this manner the studies of bulk modulus and of pressure viscosity are closely related.

The inventor's previous patent cited-above determines secant bulk modulus of fluid samples. The present invention determines targent bulk modulus from the secant bulk modulus data of the inventor's previous patent, and can further determine fluid density as a function of pressure form secant bulk modulus data.

It is an object of the invention to provide a system and method to measure both the isothermal secant and tangent bulk modulus and the density of functional fluids. The instrumentation and methodology described in this invention use much smaller volumes of fluids which permits the measurement of these critical properties on experimental fluids which are available in only limited quantities.

These and many other objects and advantages of the present invention will be readily apparent to one skilled in the pertinent art from the following detailed description of a preferred embodiment of the invention and related drawings.

DETAILED DESCRIPTION OF THE PREFERRED EMBODIMENT

The present invention includes a method and apparatus for the determination of isothermal secant and tangent bulk modulus and density as a function of pressure and temperature of functional fluids.

Figure 1:
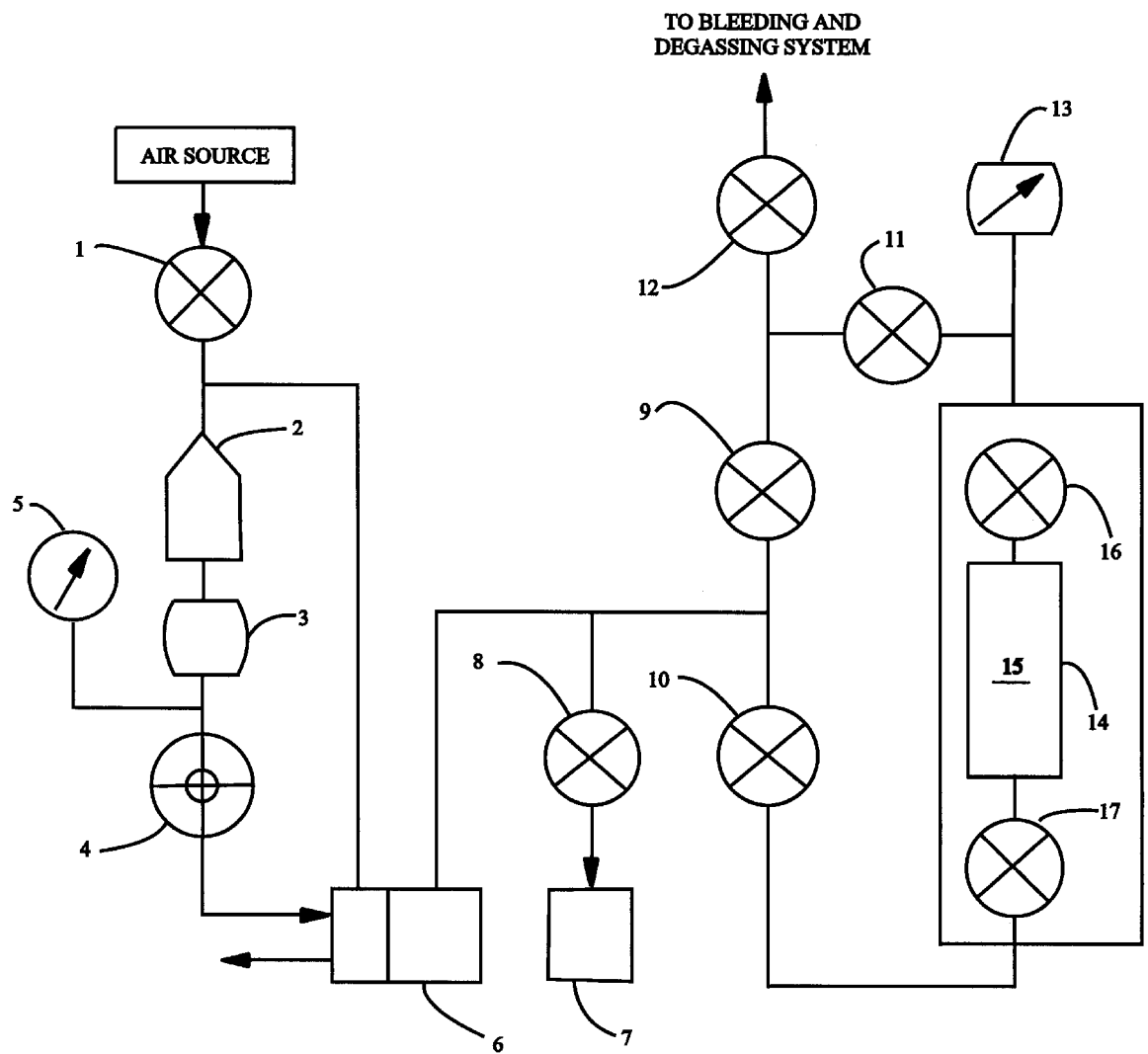
FIG. 1 is a schematic of the prior art Apparatus for the determination of Bulk Modulus and Density at elevated pressure.

FIG. 1 is a prior art system and

Figure 2:
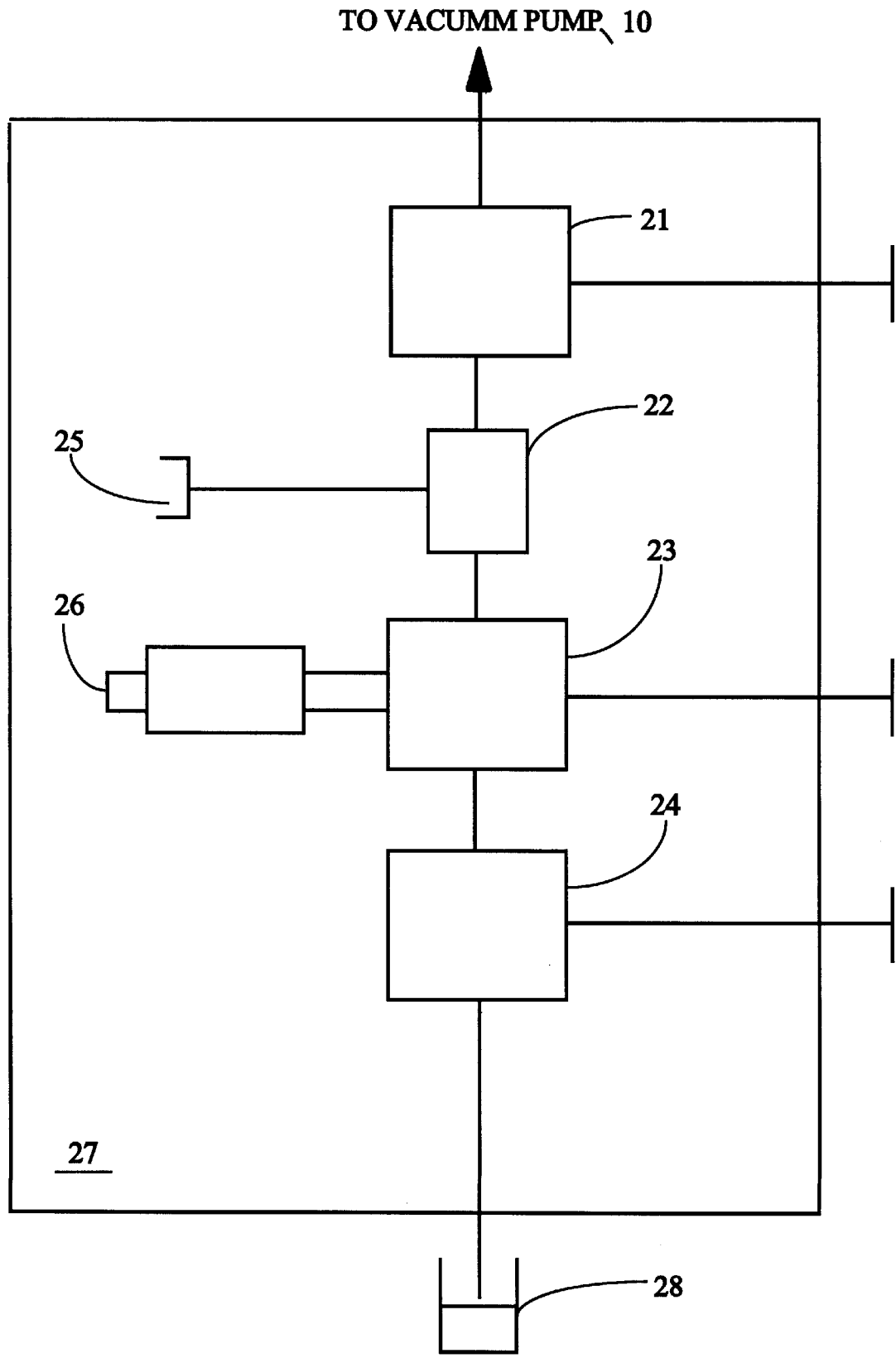
FIG. 2 shows is a schematic of the present invention.

FIG. 2 is a block diagram of the apparatus of the present invention. It includes the equipment listed in Table A.

TABLE A

Keys:
21. Top Valve
22. 22. A Tee
23. 23. Pressure Valve
24. Bottom Valve
25. Thermocouple
26. Pressure Transducer
27. Oven
28. Sample Container All fittings are m/p coned and threaded type for use at working presure up to 20,000 psig.

In FIG. 2, a fluid under test flows from the sample container 28 into the oven 27 form the bottome valve 24 and pressure valve 23 to the pressure transducer 26.

As mentioned above, FIG. 1 is a prior art system and FIG. 2 illustrates the present invention.

To explain how the test configuration of FIG. 2 works, consider the system of FIG. 1. FIG. 1 is the invention of the above-cited Krawetz patent which is for a method for the measurement of bulk modulus and pressure viscosity of liquid. The method is based on a pressure-volume-temperature relationship at a constant volume. The aooaratus comprises a constant temperature oven a container vessel within the oven, a plurality of valves, a pump, a regulator and a viscometer. The apparatus is used to obtain a relationship expressing vessel volume at any specified temperature and pressure. This relationship is then used to determine bulk modulus and pressure viscosity.

As explained in this patent, bulk modulus expresses the resistance of a fluid to compression and can be defined as the reciprocal of compressibility. This property can be determined by both static and dynamic methods. In either case, bulk modulus may be reported as the secant or tangent bulk modulus.

Secant bulk modulus (mean bulk modulus) is defined as a product of the priginal fluid volume and the slope of the secant drawn from the origin to any specified point on the p vs. DELTA V/V curve.

The system provided in FIG. 2 is designed to measure bulk modulus of a liquid and is based on a P-V-T relationship at constant volume corrected for changes in system volume due to elevated pressure and temperature. As shown in FIG. 1, the apparatus used to determine bulk modulus comprises a pressure vessel 15 in which the liquid to be tested is introduced from a tank 7 through a release valve 8, a pressure balancing valve 9 isolating valves 10 and 11, and vessel valves 16 and 17. The vessel 15, along with the valves 16 and 17 are placed in a constant temperature oven 14. The valve 12 is a bleeding valve. A transducer 13 records the pressure within the vessel 15.

The liquid in vessel 15 is pressurized by means of an air driven liquid pump 6 which is supplied with air from an air source 18 through an air valve 1, an air filter 2, a pressure regulator 3, and a speed control valve 4. The air pressure is monitored by a pressure guage 5.

In terms of the present invention, secant bulk modulus (mean bulk modulus) is defined as the product of original fluid volume and the slope of the second drawn from the point of origin to any specified point on the curve of p vs. ΔV/V.

Isothermal secant (static) bulk modulus, $\overline{B}_i$, may be expressed as:

$$\overline{B}_i = -\left[V_T^i \frac{\Delta P}{\Delta V}\right]_T = -\left[V_T^i \frac{(P_n - P_o)}{(V_n - V_T^i)}\right]_T \tag{1}$$

or $$\overline{B}_i = -\left[V_T^i \frac{P}{\Delta V}\right]_T \tag{2}$$

Since, at the origin, $P_o$ is equal to zero.

Similarly, adiabatic (dynamic or isentropic) bulk modules, $\overline{B}_a$, may be expressed as:

$$\overline{B}_a = -\left[V_T^i \frac{\Delta P}{\Delta V}\right]_S = -\left[V_T^i \frac{(P_2 - P_1)}{(V_2 - V_T^i)}\right]_S \tag{3}$$

or $$\overline{B}_a = -\left[V_T^i \frac{P}{\Delta V}\right]_S \tag{4}$$

Tangent bulk modulus is defined as the product of fluid volume at any specified pressure and the partial derivative of fluid pressure with respect to volume. Thus, Isothermal (static) tangent bulk modulus may be expressed as:

$$B_i = -\left[V_{T,P}^f \frac{\partial P}{\partial T}\right]_T \tag{5}$$

and adiabatic (dynamic or isentropic) bulk modulus may be expressed as:

$$B_s = -\left[V_{T,P}^f \frac{\partial P}{\partial T}\right]_S \tag{6}$$

The following notation has been employed in equations (1) through (6):

$\overline{B}i$=Isothermal secant bulk modulus
$\overline{B}s$=Adiabatic secant bulk modulus
$Bi$=Isothermal tangent bulk modulus
$Ba$=Adiabatic tangent bulk modulus
$V^i_T$=Volume of sample at zero pressure and temperature T, i.e. the origin.
$P_o$=Pressure at origin, psig
$P_a$=Pressure at point n, psig
$V_a$=Volume (originally V) at point n at pressure Pn and temperature T.
$V_{T,P}^f$=Actual volume of sample at pressure P and temperature T as determined by the bulk modulus (compressibility) of the sample.
P=pressure, psig
T=temperature, °C.

Isothermal Tangent Bulk Modulus as a Function of Pressure

Isothermal Secant Bulk Modulus:

$$\overline{B}_i = -V_o\left(\frac{P}{V - V_o}\right)_T \tag{7}$$

Isothermal Tangent Bulk Modulus:

$$B_i = -V\left(\frac{\partial P}{\partial V}\right)_T \tag{8}$$

At constant temperature, and pressure less than about 20,000 psig, $\overline{B}_i$ is a linear function of pressure for any fluid:

$$\overline{B}_i = \overline{B}_i^0 + CP \tag{9}$$

where:

$\overline{B}_i^0$ is the isothermal secant bulk modulus at 0 psig and C is a constant.

$$\text{Let } \delta = \frac{V_o - V}{V_o}$$

$$\delta = 1 - \frac{V}{V_o}$$

$$\text{then } \frac{\partial \delta}{\partial V} = -\frac{1}{V_o}$$

Equation (7) becomes:

$$\bar{B}_i = \left(\frac{V_o}{V_o - V}\right) P \quad (10)$$

$$\bar{B}_i = \frac{P}{\delta}$$

Equation (8) becomes:

$$B_i = -V\left(\frac{\partial P}{\partial \delta} \times \frac{\partial \delta}{\partial V}\right) \quad (11)$$

$$B_i = \frac{V}{V_o} \times \frac{\partial P}{\partial \delta}$$

$$B_i = (1-\delta)\frac{\partial P}{\partial \delta}$$

From Equations (8) and (9):

$$\frac{P}{\delta} = \bar{B}_i^o + CP \quad (12)$$

or $$P\left(\frac{1}{\delta} - C\right) = \bar{B}_i^o$$

Differentiate Eq. (12) with respect to $\delta$:

$$\frac{\partial P}{\partial \delta}\left(\frac{1}{\delta} - C\right) - \frac{P}{\delta^2} = 0 \quad (13)$$

$$\frac{\partial P}{\partial \delta} = \frac{P}{\delta^2\left(\frac{1}{\delta} - C\right)}$$

$$\frac{\partial P}{\partial \delta} = \frac{P/\delta}{1 - C\delta}$$

$$\frac{\partial P}{\partial \delta} = \frac{\bar{B}_i}{1 - C\delta}$$

Substitute (13) into (11):

$$B_i = \frac{\bar{B}_i(1-\delta)}{1 - C\delta}$$

$$B_i = \frac{\bar{B}_i(1 - P/\bar{B}_i)}{1 - C(P/\bar{B}_i)}$$

$$B_i = \frac{\bar{B}_i(\bar{B}_i - P)}{\bar{B}_i - CP}$$

Substitute (9) into (14):

$$B_i = \frac{(\bar{B}_i^o + CP)(\bar{B}_i^o + CP - P)}{\bar{B}_i^o} \quad (15)$$

$$B_i = \left[\frac{C(C-1)}{\bar{B}_i^o}\right]P^2 + (2C-1)P + \bar{B}_i^o$$

Calculation of Density from Secant Bulk Modulus

Secant Bulk Modulus is defined as:

$$\bar{B}_i = P\left(\frac{V_o}{V_o - V}\right) \quad (16)$$

where:

P=Pressure, psig
$V_0$=Volume at 0 psig
V=Volume at P psig

From (16):

$$V = \left(1 - \frac{P}{\bar{B}_i}\right)V_o \quad (17)$$

or $$\frac{1}{V} = \frac{1/V_o}{1 - P/\bar{B}_i} \quad (18)$$

or $$d = \frac{d_o}{1 - P/\bar{B}_i} \quad (19)$$

where:

$d_0$=density at 0 psig
d=density at P psig

Secant bulk modulus (mean bulk modulus) is defined as the product of original fluid volume and the slope of the secant drawn from the point of orgin to any specified point on the curve of p vs. $\Delta V/V$. Isothermal (static) bulk modulus is defined below in equation 20:

$$\bar{B} = -V_0[\Delta P/\Delta V]_T \quad (20)$$

Or when ambient pressure is taken as the basic of measurement as shown below in equation 21.

$$\bar{B}_i = -V_0 P/\Delta V \quad (21)$$

The following procedure has been successfully employed for the determination of secant bulk modulus over the pressure range from 0 to 15,000 psig. At temperatures up to 150 degrees C. Temperature is limited only by the availability of pressure transducers capable of operating at elevated temperatures. The apparatus is shown in FIG. 2. Temperature control is achieved by using the system within the oven of a gas chromatograph so that reliable and uniform operating temperature are attained over the range of –50 degrees C. to the maximum permitted by the pressure transducer.

At any temperature for a given turn number, n, $V/\Delta V$ is calculated from the definition of secant bulk modulus, $B_a$, as follows:

$$(V/\Delta V) = B_a/P = B_a/(P_a - P_o) \quad (22)$$

where:

$B_S$=secant bulk modulus at $(P_a - P_o)$ of calibrating fluid.
$P_a$=Pressure at $n^{th}$ turn.
$P_o$=Pressure at turn 0.
$(V/\Delta V)$=A constant determined by system volume and the displacement of the variable piston. It is independent of temperature.

TABLE 1

Sample Bulk Modulus Calibration

Calibration fluid: Water  
Test Condition: 40° C.  
Data from published source: International Critical Tables

| Pressure, psig | Bulk Modulus |
|---|---|
| 7349 | 354299 |
| 14697 | 382654 |

Calibration:

| Turn # | [1] P, psi | [2] Pn-Po | [3] Bs, psi | [4] V/ΔV |
|---|---|---|---|---|
| 0 | 36 | | | |
| 1 | 1318 | 1282 | 330888 | 258,10300 |
| 2 | 2681 | 2654 | 336147 | 127,08770 |
| 3 | 4084 | 4048 | 341561 | 84.37772 |
| 4 | 5531 | 5495 | 347145 | 63.17470 |
| 5 | 7022 | 6986 | 352899 | 50.51517 |
| 6 | 8549 | 8513 | 358791 | 42.14625 |
| 7 | 10129 | 10093 | 364888 | 36.15258 |

Notes:  
[1] = Pressure readings at the 0 and nth turn of the valve.  
[2] = Pressure difference between the nth turn and the 0 turn.  
[3] = Secant bulk modulus at the corresponding pressure in column [2], interpolated or extrapolated from the data published in the International Critical Tables.  
[4] = Volume constant of the system at the nth turn, equals secant bulk modulus divided by the corresponding pressure.

After (V/ΔV) has been determined, isothermal secant bulk modulus of unknown sample is obtained from measured values of (Pn−Po) at various turns of the variable piston as follows:

$$\bar{B}_t = (Pn-Po)(V/\Delta V) \quad (23)$$

It should be noted that since the calibration factor (V/ΔV) is a ratio of volumes it is a unit-less factor which is essentially independent of temperature.

TABLE 2

Sample Secant Bulk Modulus Determination

Lab. No. MLO-90-54  
Test Condition: 40° C.  
Calibration fluid: Water at 40° C.

| Turn # | [1] P, psi | [2] Pn-Po | [3] V/ΔV | [4] Bs, psi |
|---|---|---|---|---|
| 0 | 36 | | | |
| 1 | 825 | 789 | 258,10300 | 203644 |
| 2 | 1661 | 1625 | 127,08770 | 206518 |
| 3 | 2545 | 2509 | 84.37772 | 211704 |
| 4 | 3473 | 3437 | 63,17470 | 217132 |
| 5 | 4448 | 4412 | 50.51517 | 222873 |
| 6 | 5470 | 5434 | 42.14625 | 229023 |
| 7 | 6539 | 8503 | 36.15258 | 235101 |

Notes:  
[1] = Pressure readings at the 0 and nth turn of the valve.  
[2] = Pressure difference between the nth turn and the 0 turn.  
[3] = Volume constant of the system at the nth turn, see the calibration sheet.  
[4] = Secant bulk modulus at the corresponding pressure in column [2], equals pressure multiplied by the volume constant.

While the invention has been described in its presently preferred embodiment it is understood that the words which have been used are words of description rather than words of limitation and that changes within the purview of the appended claims may be made without departing from the scope and spirit of the invention in its broader aspects.

We claim:

1. In a system for measuring the isothermal adiabatic bulk modulus $\bar{B}_S$ of a liquid in a vessel on a pressure-volume-temperature relationship at a constant volume corrected for changes in vessel volume due to elevated pressure and temperature, a method comprising the steps of:

entirely filling said vessel with said liquid;

degassing said vessel calibrating the volume of the vessel at various pressures and temperatures from atmospheric pressure and ambient temperature to various elevated temperatures and pressures to determine data relative to the final volume $V_{T,P}^f$, at any given pressure and temperature, and using said data to establish a calibration curve;

determining the volume $V_T$ of the vessel at atmospheric pressure and temperature T;

determining the weight $W_T$ of the liquids at temperature T and 1 atmosphere;

determining the density $D_T$ of the liquid at temperature T and 1 atmosphere; determining the volume determining the volume $V_{T,P}^f$, where $V_{T,P}^f$, is the volume of the liquid at temperature T;

determining the volume $V_T^1$ of the vessel at temperature T and 1 atmosphere;

solve the equation $$\bar{B}_S = -[V_{T,P}^f \, \partial P/\partial T]_S$$

where ∂P is equal to the difference in pressure P between 1 atmosphere and a specified pressure; and ∂T is a change in temperature;

calibrating the volume of the vessel at various pressures and temperatures from atmospheric pressure and ambient temperature to various elevated temperature and pressures to determine the volume, and establishing a calibration curve.

* * * * *